United States Patent
Ramasamy et al.

(10) Patent No.: US 7,371,857 B2
(45) Date of Patent: May 13, 2008

(54) SYNTHESIS FOR HYDROXYALKYLATED HETEROCYCLIC BASES

(75) Inventors: Kanda Ramasamy, Aliso Viejo, CA (US); Jean-Luc Girardet, Aliso Viejo, CA (US); Haoyun An, Carlsbad, CA (US); Zhi Hong, Aliso Viejo, CA (US); Robert Orr, San Clemente, CA (US)

(73) Assignee: Valeant Research & Development, Costa Mesa, CA (US)

( * ) Notice: Subject to any disclaimer, the term of this patent is extended or adjusted under 35 U.S.C. 154(b) by 82 days.

(21) Appl. No.: 10/523,938

(22) PCT Filed: Aug. 8, 2002

(86) PCT No.: PCT/US02/25540

§ 371 (c)(1),
(2), (4) Date: Oct. 21, 2005

(87) PCT Pub. No.: WO2004/014912

PCT Pub. Date: Feb. 19, 2004

(65) Prior Publication Data

US 2006/0135768 A1 Jun. 22, 2006

(51) Int. Cl.
*C07D 473/34* (2006.01)
*C07F 9/6561* (2006.01)

(52) U.S. Cl. ........................ 544/244; 544/277
(58) Field of Classification Search ............ None
See application file for complete search history.

(56) References Cited

U.S. PATENT DOCUMENTS

| 5,514,798 A | 5/1996 | Bischofberger et al. |
| 5,686,629 A * | 11/1997 | Bischofberger et al. .... 549/229 |
| 5,935,946 A * | 8/1999 | Munger et al. ............ 514/81 |

FOREIGN PATENT DOCUMENTS

| JP | 2001-213867 | 8/2001 |
| JP | 2001213867 A * | 8/2001 |

OTHER PUBLICATIONS

Lubczak, R. "Reactions of Adenine with Ethylene Oxide and Propylene Oxide" *Journal of Applied Polymer Science*, 2002, pp. 489-497, vol. 86.

* cited by examiner

*Primary Examiner*—Mark L Berch
(74) *Attorney, Agent, or Firm*—Saliwanchik, Lloyd & Saliwanchik

(57) ABSTRACT

A hydroxyalkylated heterocyclic base is prepared by reacting a heterocyclic base with an alkylene carbonate in dimethylacetamide as a solvent, wherein the hydroxyalkylated heterocyclic base is isolated from the solvent using isopropanol or tert-butylmethylether.

16 Claims, 5 Drawing Sheets

| Solvent | Dilution (D) and Washing (W) | Yield(%) | $N_9 - N_7$ Isomers | Temp | NaOH |
|---|---|---|---|---|---|
| DMF | D: Toluene<br>W: Toluene/Acetone | 96% | $N_9$-(79%); $N_7$-(18%) | 160°C | + |
| DMF | D: Toluene<br>W: Toluene/Acetone | 93% | $N_9$-(77%); $N_7$-(19%) | 150°C | + |
| DMF | D: Toluene<br>W: Toluene/Acetone, crystallize | 70% | $N_9$-(97%); $N_7$-(1.5%)<br>Crystals from EtOH | 160°C | + |
| DMF | D: Toluene<br>W: Toluene/EtOH(cold) | 67% | $N_9$-(91%); $N_7$-(3.3%) | 150°C | + |
| DMF | D: Toluene<br>W: Toluene/Acetone, crystallize | 56% | $N_9$-(98%); $N_7$-(1.56%)<br>Crystals from EtOH | 130°C | NaOEt |
| DMF | D: Toluene<br>W: Toluene/EtOH(cold) | 95% | $N_9$-(55%); $N_7$-(12%)<br>Un-reacted starting | 160°C | - |
| DMF | D: Toluene<br>W: Toluene/EtOH(cold) | 70% | $N_9$-(83%); $N_7$-(6%) | 150°C | - |
| DEF | D: Toluene<br>W: Toluene/EtOH(cold) | 89% | $N_9$-(77%); $N_7$-(21%) | 150°C | + |
| DMA | D: Toluene<br>W: Toluene/EtOH(cold) | 70% | $N_9$-(85%); $N_7$-(6%) | 150°C | + |
| DMA | D: Toluene<br>W: Toluene/EtOH(cold) | 84% | $N_9$-(73%); $N_7$-(19.5%) | 150°C | - |

Table 1

Figure 1

| Solvent | Dilution (D) and Washing (W) | Yield(%) | $N_9 - N_7$ Isomers | Temp | NaOH |
|---|---|---|---|---|---|
| DMA | D: None, evaporated to dryness and t-BME added<br>W: t-BME | 100% | $N_9$-(76%); $N_7$-(20%) | 150°C | + |
| DMA | D: None, evaporated to dryness and $CH_3CN$ added<br>W: $CH_3CN$ | 92% | $N_9$-(80%); $N_7$-(16%) | 150°C | + |
| DMA | D: None, evaporated to dryness and EtOH added<br>W: EtOH | 67% | $N_9$-(90%); $N_7$-(4%) | 150°C | + |
| DMA | D: None, evaporated to dryness and IPA added<br>W: IPA | 84% | $N_9$-(92%); $N_7$-(3%) | 150°C | + |
| DMA | D: None, evaporated to dryness and IPA/CH3CN (1:1) added<br>W: IPA/CH3CN (1:1) | 91% | $N_9$-(95.25%); $N_7$-(2.49%) | 150°C | + |
| DMA | D: Evaporated to half in volume and Toluene added<br>W: Toluene/ EtOH(cold) | 87% | $N_9$-(76%); $N_7$-(12%) | 160°C | + |
| DMA | D: Evaporated to half in volume and Toluene added<br>W: Toluene/ EtOH(cold) | 89% | $N_9$-(68%); $N_7$-(15%) | 140°C | + |

Table 2

Figure 2

| Solvent | Dilution (D) and Washing (W) | Yield(%) | $N_9 - N_7$ Isomers | Temp | Cat |
|---|---|---|---|---|---|
| DMA | D: $CH_3CN$<br>W: $CH_3CN$ | 94% | $N_9$-(88%); $N_7$-(11%) | 150°C | + |
| DMA | D: EtOAc<br>W: EtOAc | 89% | $N_9$-(90%); $N_7$-(8%) | 150°C | + |
| DMA | D: Toluene<br>W: Toluene/EtOH (cold) | 95% | $N_9$-(92%); $N_7$-(7.5%) | 150°C | + |
| DMA | D: Toluene<br>W: IPA (cold) | 97% | $N_9$-(86%); $N_7$-(13%) | 150°C | + |
| DMA | D: IPA<br>W: IPA (cold) | 91% | $N_9$-(97%); $N_7$-(1.34%) | 150°C | + |
| DMA | D: IPA<br>W: IPA | 87% | $N_9$-(97%); $N_7$-(1.15%) | 160°C | + |
| DMA | D: IPA<br>W: IPA | 82% | $N_9$-(98%); $N_7$-(0.96%) | 140°C | + |
| DMA | D: t-BME<br>W: IPA | 87% | $N_9$-(95.4%); $N_7$-(2.78%) | 150°C | + |
| DMF | D: Toluene<br>W: Toluene/EtOH (cold) | 93% | $N_9$-(91%); $N_7$-(3%) | Reflux | + |

Table 3

Figure 3

HPLC METHOD

| | |
|---|---|
| Column | SYNERGI 5 µ, 150 x 4.6 mm Phenomenex (C18) |
| Mobile Phase | A  20 mM KH$_2$PO$_4$ pH 6.2 Buffer (KOH) |
| | B  Acetonitrile |
| Flow Rate | 1.00 mL/min |

| Gradient Table | 0-15 min | 0-60% B |
|---|---|---|
| | 15-17 min | 60-0% B |
| | 17-19 min | 0% B |

| | |
|---|---|
| Column Temperature | 35 °C |
| Sample Temperature | 6 °C (Autosampler) |
| Sample Concentration | 0.5 mg/mL (Water) |
| Injection Volume | 10 µL |
| Detection Wavelength | 220, 270 nm |

Figure 4

SYNTHESIS FOR HYDROXYALKYLATED HETEROCYCLIC BASES

FIELD OF THE INVENTION

The field of the invention is synthesis of modified heterocyclic bases and especially relates to synthesis of hydroxyalkylated natural and modified nucleobases.

BACKGROUND OF THE INVENTION

Use of various nucleoside analogs, and especially acyclic nucleoside analogs in treatment of neoplastic diseases and viral infections has recently gained considerable attention (see e.g., Murono et al. in Cancer Res. 2001 Nov. 1; 61(21):7875-7, or Sekiya et al. in J. Med. Chem. 2002 Jul. 4; 45(14):3138-42). Consequently, synthesis of such nucleoside analogs via hydroxyalkylated heterocyclic bases as key intermediates has become increasingly important, and various methods of preparing hydroxyalkylated heterocyclic bases are known in the art.

For example, Ueda et al. reported the synthesis of 9-hydroxyethyladenine from a reaction in which ethyl carbonate was reacted with adenine using N,N-dimethylformamide (also known as dimethylformamide or DMF) as the solvent (Die Makromolekulare Chemie 1968, 120, 12-20 (Nr.2839)). However, under the conditions employed (i.e., complete removal of the solvent to dryness and recrystallization from ethanol), the total yield of the desired product was only 54%. Moreover, Ueda's conditions led to significant formation of the N7-alkylated byproduct.

In a similar approach, described in U.S. Pat. No. 5,514,798 to Bischofberger et al., which is incorporated herein by reference, 9-hydroxyethyladenine is produced in a reaction between ethyl carbonate and adenine using DMF as a solvent, and the inventors employed a non-polar solvent (toluene) to drive the reaction product from the solvent. While Bischofberger's approach significantly improved the total yield, specificity of the reaction towards the desired N9-hydroxyalkylated product was relatively low and therefore typically required an additional separation step before the reaction product could be employed in further derivatization reactions.

Alternatively, alkylation of a heterocyclic base may be performed following a Mitsunobo reaction as described in U.S. Pat. No. 5,874,577 to Chen et al., wherein linear synthesis starts from 1,3-dioxolane that is subsequently acetylated. Phosphorus is introduced into the so prepared intermediate via reaction with triethoxyphosphine, and the resulting alkylene phosphonate is converted to the corresponding hydroxyalkylene phosphonate, which is then coupled to the heterocyclic base in a Mitsunobu reaction. While Chen's reaction advantageously provides the desired phosphonate nucleoside analog without a hydroxyalkylated intermediate, the total yield was only about 10%, with a selectivity of the Mitsunobu reaction towards the N9-atom of the adenine of only 43%. Similar reaction sequences were reported in Collect. Czech. Chem. Commun. 1989, 54(8), 2190-2210, and in Collect. Czech. Chem. Commun. 1987, 52(11), 2801-2809 with comparable total yields of about 10%, and, depending on the particular conditions, selectivity towards N9-alkylation of the adenine, of between about 11-60%.

Although various methods are known in the art to synthesize various hydroxyalkylated heterocyclic bases, all or almost all of them suffer from one or more disadvantages. Therefore, there is still a need to provide improved synthetic protocols for preparation of hydroxyalkylated heterocyclic bases.

SUMMARY OF THE INVENTION

The present invention is directed to methods of preparing an alkylated heterocyclic base at conditions that allow relatively high yields of the product at high selectivity over a byproduct. In a particularly contemplated aspect of the inventive subject matter, a heterocyclic base of Structure 1 is reacted in dimethylacetamide with a compound of Structure 2 to form a product according to Structure 3

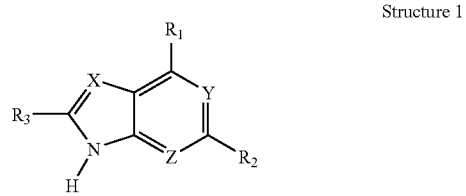

Structure 1

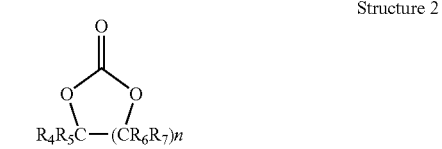

Structure 2

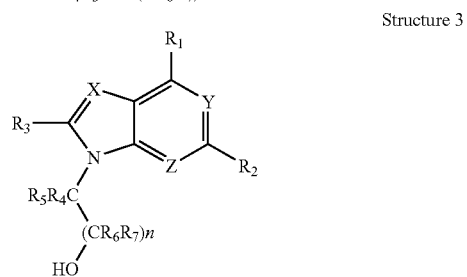

Structure 3 wherein X, Y and Z are independently N or CR, with R being H, halogen, OH, $NH_2$, or substituted or unsubstituted alkyl, alkenyl, alkynyl, aryl, or alkaryl; wherein $R_1$, $R_2$, $R_3$, $R_4$, $R_5$, $R_6$, and $R_7$ are independently H, halogen, OH, $NH_2$, $CO(NH_2)$, $CNH(NH_2)$, $N_3$, or substituted or unsubstituted alkyl, alkenyl, alkynyl, aryl, or alkaryl; wherein n is an integer between 1 and 3; and wherein Structure 3 is isolated from the dimethylacetamide using isopropanol or tert-butylmethylether.

In another aspect of the inventive subject matter, X, Y and Z are N, and wherein $R_1$ is $NH_2$, $R_2$ and $R_3$ are H, and/or $R_4$, $R_5$, $R_6$, and $R_7$ are H, and wherein n is 1. Furthermore, it is generally preferred that the product according to structure 3 is isolated from the solvent (dimethylacetamide) using isopropanol. With respect to the reaction temperature it is generally preferred that the temperature is no less than 150 centigrade, and even more preferably no less than 160 centigrade. Still further, while the reaction may be performed without a catalyst, it is preferred that a basic catalyst (e.g., NaOH) is employed.

In yet another aspect of the inventive subject matter, X is N, and the step of reacting the heterocyclic base according to Structure 1 with the compound according to Structure 2 further leads to an N7-alkylated byproduct according to Structure 4 (with the substituents as defined as in Structures 1-3 above)

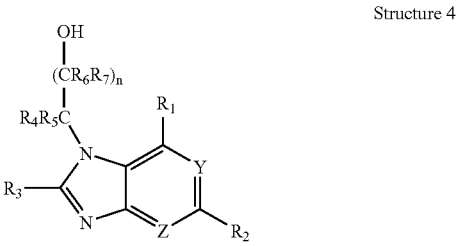

Structure 4

In such reactions, and depending on the particular reaction conditions, it is contemplated that the step of reacting the heterocyclic base with the compound gives (1) a total yield of the product and the N7-alkylated byproduct of at least 82%, and wherein about 98% of the total yield is the product and wherein about 1% of the total yield is the N7-alkylated byproduct, (2) a total yield of the product and the N7-alkylated byproduct of at least 87%, and wherein about 97% of the total yield is the product and wherein about 1.1% of the total yield is the N7-alkylated byproduct, or (3) a total yield of the product and the N7-alkylated byproduct of at least 91%, and wherein about 97% of the total yield is the product and wherein about 1.3% of the total yield is the N7-alkylated byproduct.

In still further contemplated aspects, the concentration of the heterocyclic base present in the dimethylacetamide is at least 220 mM, and more preferably at least 270 mM, and it is still further contemplated that the product according to Structure 3 with a phosphonate, which may have a structure according to Structure 5

Structure 5 in which L is a leaving group (e.g., tosyl group), and wherein W is a protecting group of the oxygen (e.g., ethyl group). Such reactions may be particularly useful where the product according to Structure 3 is employed as an intermediate in the synthesis of PMEA.

Various objects, features, aspects and advantages of the present invention will become more apparent from the following detailed description of preferred embodiments of the invention, along with the accompanying drawings.

BRIEF DESCRIPTION OF THE DRAWING

FIG. 1 is a table depicting total yield and selectivity of contemplated reaction products in dependence on the reaction solvent and other parameters.

FIG. 2 is a table depicting total yield and selectivity of contemplated reaction products in dependence on evaporation, wash solvent and other parameters.

FIG. 3 is a table depicting total yield and selectivity of contemplated reaction products in dependence on the reaction, dilution, and wash solvent and other parameters.

FIG. 4 is a Table summarizing the HPLC conditions for separation of reaction products.

DETAILED DESCRIPTION

Figure 5:
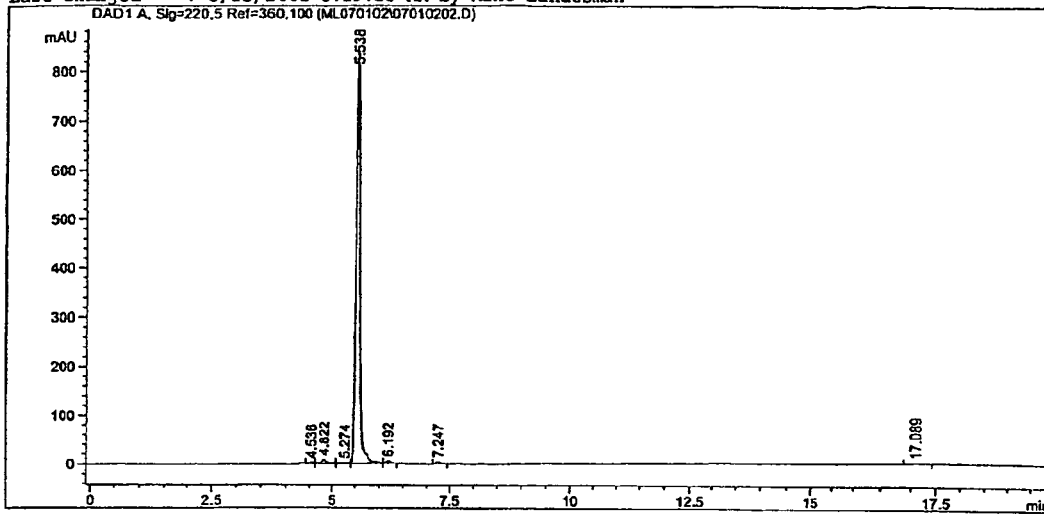
FIG. 5 is a typical elution profile using the HPLC conditions of Table 4

The inventors surprisingly discovered that hydroxyalkylated heterocyclic bases may be prepared at conditions that allow relatively high yields of the desired product and very high selectivity over a byproduct of the reaction by using particular solvents for both the reaction and the dilution/wash step.

In one especially preferred aspect, adenine as a heterocyclic base is reacted with ethyl carbonate in dimethylacetamide to form N9-hydroxyethyladenine at high yield and selectivity over the byproduct N7-hydroxyethyladenine as depicted below in Scheme 1, wherein the N9-hydroxyethyladenine is isolated (via dilution of the reaction solvent and subsequent washes of the precipitate) from the dimethylacetamide using isopropanol or tert-butylmethylether.

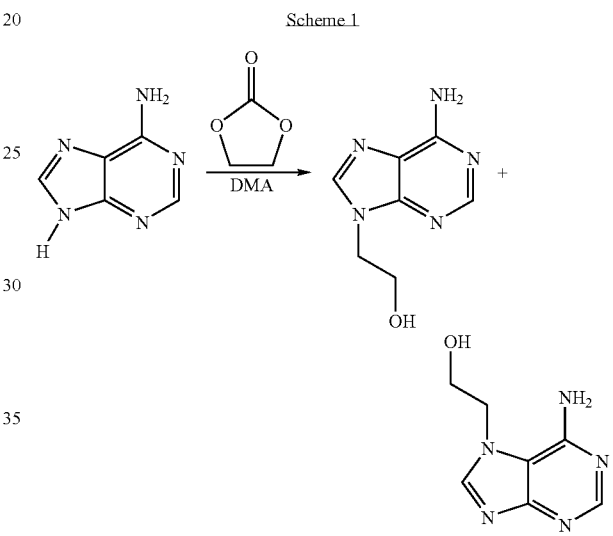

Scheme 1

While it is generally contemplated that the above procedure is particularly suitable for adenine as a heterocyclic base, it should be recognized that numerous alternative heterocyclic bases may also be employed. The term "heterocyclic base" as used herein refers to any compound in which a plurality of atoms form a ring via a plurality of covalent bonds, wherein the ring includes at least one atom other than a carbon atom.

Particularly contemplated alternative heterocyclic bases include those in which a 5-membered ring is fused to a 6-membered ring (e.g., purine, pyrrolo[2,3-d]pyrimidine), and those in which a 6-membered ring is fused to another 6-membered or higher ring (e.g., pyrido[4,5-d]pyrimidine, benzodiazepine). Moreover, contemplated heterocyclic bases may further be substituted in one or more positions. The term "substituted" as used herein refers to a replacement of an atom or chemical group (e.g., H, $NH_2$, or OH) with a functional group, and particularly contemplated functional groups include nucleophilic groups (e.g., —$NH_2$, —OH, —SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3+$), halogens (e.g., —F, —Cl), and all chemically reasonable combinations thereof.

For example, especially suitable heterocyclic bases will have a structure according to Structure 1

Structure 1

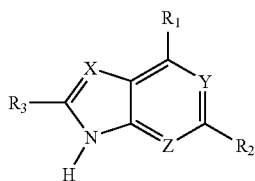

wherein X, Y and Z are independently N or CR, with R being H, halogen, OH, $NH_2$, or substituted or unsubstituted alkyl, alkenyl, alkynyl, aryl, or alkaryl; wherein $R_1$, $R_2$, and $R_3$ are independently H, halogen, OH, $NH_2$, $CO(NH_2)$, $CNH(NH_2)$, $N_3$, or a substituted or unsubstituted alkyl, alkenyl, alkynyl, aryl, or alkaryl. It is still further preferred that the concentration of the heterocyclic base is relatively high. Consequently, and depending on the reaction solvent it is preferred that the concentration of the heterocyclic base may be up to 220 mM, and more preferably at least 270 mM (especially where dimethylacetamide is the solvent).

Similarly, it should be recognized that the alkylating reagent need not necessarily be limited to ethyl carbonate, and depending on the length and chemical composition, the alkyl portion in the alkyl carbonate may vary substantially. For example, the alkyl portion may include one or more substituents, and may have more than two carbon atoms. Therefore, particularly suitable alkylating reagents will have a structure according to Structure 2

Structure 2

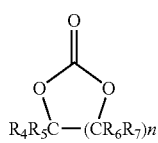

wherein $R_4$, $R_5$, $R_6$, and $R_7$ are independently H, halogen, $N_3$, OH, $NH_2$, $CO(NH_2)$, $CNH(NH_2)$, or substituted or unsubstituted alkyl, alkenyl, alkynyl, aryl, or alkaryl, and n is an integer between 1 and 3. However, it is generally preferred that in reactions according to Scheme 1 above X, Y and Z are N, and $R_1$ is $NH_2$, $R_2$ and $R_3$ are H, and/or that $R_4$, $R_5$, $R_6$, and $R_7$ are H, wherein n is 1.

With respect to suitable solvents for the reaction, it should be recognized that the preferred solvent is dimethylacetamide (i.e. DMA). However, various alternative solvents and solvent mixtures (which may or may not include DMA) are also contemplated, and especially suitable alternative solvents include diethylformamide (i.e., DEF) and DMF. Furthermore, suitable solvents for the reaction may include a catalyst, and a particularly preferred class of catalyst is basic catalysts. An exemplary basic catalyst frequently employed for the reaction according to Scheme 1 above is NaOH.

Furthermore, the range of suitable temperatures for reacting the heterocyclic base with the alkylating agent may vary, and will depend at least in part on the presence of a catalyst and the particular solvent (combination) employed. Therefore, suitable reaction temperatures will generally be in the range of room temperature to the boiling point of the solvent (under reflux). However, it is generally preferred that the reaction includes heating to a temperature of no less than 150 centigrade (e.g., 150 to 159 centigrade), and even more preferably of no less than 160 centigrade (e.g., 160 to 166 centigrade).

In yet further contemplated aspects, and especially where in the heterocyclic base of structure 1 the atom X is N, it should be recognized that the reaction will also lead to the formation of an N7-alkylated byproduct according to Structure 4 (with the substituents Z, Y, and $R_1$-$R_7$ and n as defined above).

Structure 4

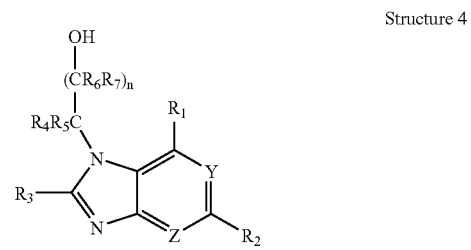

Depending on the particular reaction conditions (e.g., reaction solvent was DMA, temperature 150 centigrade, NaOH as catalyst, and isopropanol (i.e., IPA) as dilution and wash solvent), the inventors achieved a total yield of the desired N9-alkylated product and the N7-alkylated byproduct of at least about 88% (+/−1% absolute), and more typically at least about 91% (+/−1% absolute), wherein about 95% (+/−1% absolute), and more typically 97% (+/−1% absolute) of the total yield was the desired product and about 1.3% (+/−0.5% absolute) of the total yield was the N7-alkylated byproduct. The term "+/−1% absolute" as used herein means that the numeric percent value to which the term refers may vary up or down one percent. For example, 10% (+/−1% absolute) refers to a range including 9% and 11%.

With slightly modified reaction conditions (e.g., reaction solvent was DMA, the temperature 160 centigrade, NaOH as catalyst, and IPA as dilution and wash solvent), the inventors achieved a total yield of the desired N9-alkylated product and the N7-alkylated byproduct of at least 85% (+/−1% absolute), more typically 87% (+/−1% absolute), wherein about 95% (+/−1% absolute), and more typically 97% (+/−1% absolute) of the total yield was the desired product and about 1.1% (+/−0.5% absolute) of the total yield was the N7-alkylated byproduct. Similarly (e.g., reaction solvent was DMA, the temperature 140 centigrade, NaOH as catalyst, and IPA as dilution and wash solvent), the inventors achieved a total yield of the desired N9-alkylated product and the N7-alkylated byproduct of at least 80% (+/−1% absolute), and more typically 82% (+/−1% absolute), wherein about 96% (+/−1% absolute), and more typically 98% (+/−1% absolute) of the total yield was the desired product and about 0.9% (+/−0.5% absolute) of the total yield was the N7'-alkylated byproduct.

With respect to the isolation of the desired N9-alkylated product from the reaction solvent, it is contemplated that isolation may be performed in various manners, including evaporation of the reaction solvent and crystallization or precipitation from the reaction solvent by diluting the reaction solvent with a dilution solvent. Especially preferred dilution solvents are relatively polar solvents, and particularly preferred dilution solvents are isopropanol and tert-butylmethylether (i.e., tBME or MTBE).

Alternatively, the inventors contemplate that the heterocyclic base may also be hydroxyalkylated to the desired product by reacting the heterocyclic base with ethylene oxide. In such reactions, it is contemplated that at least a significant fraction (i.e., at least 50%, more typically at least 70%) of the reaction product is the desired 9-hydroxyalkylated product While not limiting to the inventive subject matter, it is generally preferred that the solvent for such reaction is dimethylacetamide. However, it should be appreciated that various alternative solvents are also considered suitable, and all of the known solvents and solvent mixtures are contemplated for use herein.

It is still further contemplated that one or more further reactions may be performed to react the N9-alkylated product to give 9-[2-(phosphonomethoxy)ethyl]adenine (PMEA). For example, it is contemplated that the N9-alkylated product may be reacted with a phosphonate having a structure according to Structure 5

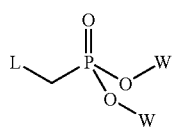

Structure 5 wherein L is a leaving group (e.g., tosyl group), and wherein W is a protecting group of the oxygen (e.g., ethyl group). For suitable reactions and conditions, see e.g., U.S. Pat. No. 5,514,798.

Thus, a method of preparing a compound having Structure 3 (see above) will have one step in which a heterocyclic base having Structure 1 (see above) is reacted with a compound having Structure 2 (see above) in dimethylacetamide to form a product according to Structure 3, wherein the radicals and atoms are defined as above, and wherein the compound is isolated from the dimethylacetamide solvent using isopropanol or tert-butylmethylether. It should be especially recognized that by using DMA as a reaction solvent the overall cost for preparation of the hydroxyalkylated product may be significantly reduced. Moreover, due to the increased solubility of various heterocyclic bases (and especially adenine) in DMA and the relatively high boiling point of DMA, the demand for a solvent may be further reduced and operational safety increased. Where DMA is employed as reaction solvent, it should further be appreciated that relatively polar solvents (e.g., IPA, or tBME) may be used to crystallize out the hydroxyalkylated product. Consequently, the above factors surprisingly allowed the inventors to generate a hydroxyalkylated heterocyclic base with high yields and selectivity (over production of the N7-alkylated byproduct).

EXPERIMENTS

The inventors performed numerous reactions between various alkylene carbonates and various heterocyclic bases using selected solvents and predetermined conditions (e.g., with or without catalyst, varied temperature, etc.), to optimize total yield and reaction selectivity (i.e., selectivity of the alkylation towards the N9 nitrogen over other position, and especially over the N7 nitrogen where present) of the alkylation reaction between ethylene carbonate and adenine as depicted in Scheme 2 below.

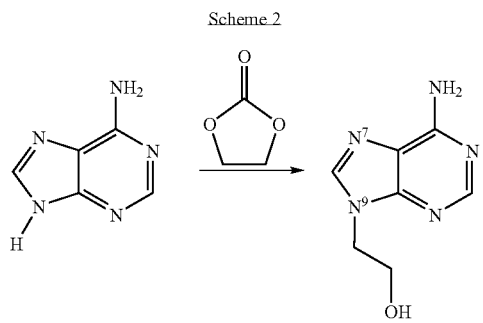

Scheme 2

In general, a mixture of alkylene carbonate (11.0 mmole), the heterocyclic base (10.0 mmole) and solid NaOH (0.5 mmol) in a solvent (e.g., DMA) (20 ml) was heated at 150° C. for 3 h. Then, the solvent was either evaporated and the residue taken up with a wash solvent, or diluted with a first solvent to precipitate the reaction products followed by a wash step with a wash solvent or wash solvent mixture (optionally followed by crystallization from a crystallization solvent).

Analysis of the reaction products was performed using HPLC and conditions as described in FIG. 4, and a typical elution profile using such HPLC conditions is shown in FIG. 5. Selected results of various reaction conditions, solvents, and wash/crystallization procedures are shown in Tables 1-3. For better visualization of the numerical differences in selectivity and yield, the following grayscale of Table A was used:

TABLE A

| Total Yield (in %) | Shade | Selectivity (as % N9 alkylated product) |
|---|---|---|
| 50-64 | | Less than 76 |
| 65-74 | | 77-83 |
| 75-84 | | 84-87 |
| 85-90 | | 88-90 |
| 91-95 | | 91-96 |
| 96-100 | | 97-100 |

Interestingly, as can be seen from Table 1 of FIG. 1, when the solvent for dilution and crystallization was, or contained an aprotic and a polar solvent (here: toluene), and when DMF was used as a reaction solvent (and further depending on reaction temperature and workup), either the total yield was desirable at relatively undesirable selectivity, or the selectivity was desirable at relatively undesirable total yield. Replacement of the reaction solvent DMF with alternative solvents (shown here: DEF and DMA) appeared to improve the disparity between total yield and selectivity in a relatively unpredictable manner. Moreover, where the disparity between total yield and selectivity improved, total yields and selectivities were generally lower and frequently were at undesirable levels.

After numerous further modifications (data not shown), the inventors eliminated the step of dilution of the reaction solvent by evaporation to force the reaction product from the solvent, and exemplary data on total yield and selectivity are shown in Table 2 of FIG. 2. These data suggested that elimination of the dilution step tended to increase the total yield to at least some degree. However, improvement of the selectivity while maintaining relatively high total yields was inconsistent.

In still further experiments, the inventors replaced the non-polar solvents for dilution of the reaction solvent with relatively high polar solvents (IPA, ethyl acetate, acetonitrile, etc.) when DMA was used as a reaction solvent. Surprisingly, and especially where DMA was the reaction solvent and IPA was the dilution and wash solvent, consistent high yields at high selectivity could be achieved under several reaction conditions as shown in the exemplary data on total yield and selectivity in Table 3 of FIG. 3. Specifically, the total yield of product was as high as 91% at an N9-alkylated product content of 97% and an N7-alkylated byproduct content of 1.34% (with NaOH as catalyst and 150 centigrade reaction temperature). Similarly, the total yield of product was as high as 87% at an N9-alkylated product content of 97% and an N7-alkylated byproduct content of 1.15% (with NaOH as catalyst and 160 centigrade reaction temperature), and the total yield of product was as high as 82% at a N9-alkylated product content of 98% and a N7-alkylated byproduct content of 0.96% (with NaOH as catalyst and 140 centigrade reaction temperature).

Moreover, by using DMA as a reaction solvent various advantages other than higher total yield and an increase of selectivity may be achieved. Among other things, the solubility of various heterocyclic bases, and especially adenine, is significantly increased as shown in Table B below.

TABLE B

| Solvent | Solubility at RT | Solubility at 150° C. |
|---|---|---|
| DMF | 2.90 mg/ml | 29.0 mg/ml |
| DEF | 1.36 mg/ml | 13.9 mg/ml |
| DMA | 4.00 mg/ml | 37.0 mg/ml |

Consequently, overall consumption of solvent may be significantly reduced by virtue of the increased solubility of the heterocyclic base in DMA (at least compared to DMF as reaction solvent), which in turn reduces the cost of preparing the alkylated heterocyclic base Still further, due to the higher boiling point of DMA as compared to DMF (166.1 Centigrade as compared to 155 Centigrade, respectively) the reaction may be performed at a temperature that is further away from the boiling point of the reaction solvent, which increases the operational safety of the reaction. Moreover, while addition of a basic catalyst is generally not required, a basic catalyst, and preferably NaOH will benefit the total yield and selectivity.

Thus, specific embodiments and applications of improved synthesis for hydroxyalkylated heterocyclic bases have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of preparing a compound according to Structure 3 comprising:

reacting a heterocyclic base according to Structure 1 with a compound according to Structure 2 in dimethylacetamide to form a product according to Structure 3;

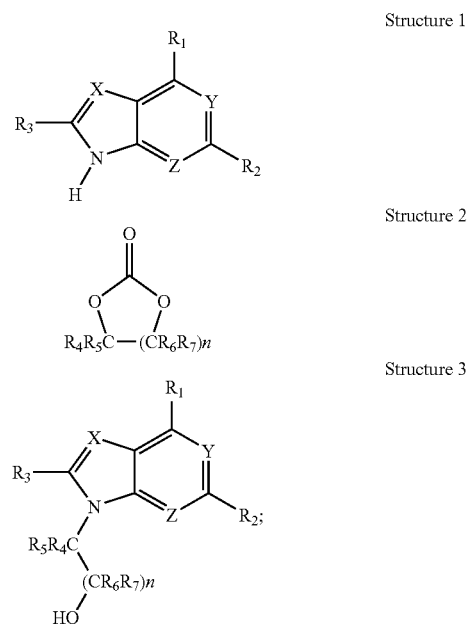

wherein X, Y and Z are N;
wherein $R_1$ is $NH_2$;
wherein $R_2$ is H;
wherein $R_3$ is H;
wherein $R_4$, $R_5$, $R_6$, and $R_7$ are independently H, halogen, OH, $NH_2$, $CO(NH_2)$, $CNH(NH_2)$, $N_3$, or substituted or unsubstituted alkyl, alkenyl, alkynyl, aryl, or alkaryl;
wherein n is an integer between 1 and 3; and
isolating Structure 3 from the dimethylacetamide solvent using isopropanol or tert-butylmethylether.

2. The method of claim 1 wherein $R_4$, $R_5$, $R_6$, and $R_7$ are H, and wherein n is 1.

3. The method of claim 1 wherein Structure 3 is isolated from the dimethylacetamide solvent using isopropanol.

4. The method of claim 1 wherein the step of reacting includes heating of the heterocyclic base according to Structure 1 and the compound according to Structure 2 to a temperature of no less than 150 centigrade.

5. The method of claim 1 wherein the step of reacting includes heating of the heterocyclic base according to Structure 1 and the compound according to Structure 2 to a temperature of no less than 160 centigrade.

6. The method of claim 1 wherein the step of reacting is performed in the presence of a basic catalyst.

7. The method of claim 6 wherein the basic catalyst is NaOH.

8. The method of claim 1 wherein X is N, and wherein the step of reacting the heterocyclic base according to Structure 1 with the compound according to Structure 2 further leads to an N7-alkylated byproduct according to Structure 4

Structure 4

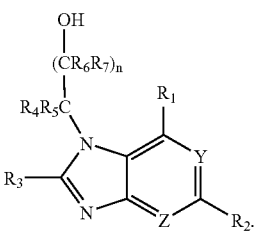

9. The method of claim 8 wherein the step of reacting the heterocyclic base with the compound gives a total yield of the product and the N7-alkylated byproduct of at least 82%, and wherein about 98% of the total yield is the product and wherein about 1% of the total yield is the N7-alkylated byproduct.

10. The method of claim 8 wherein the step of reacting the heterocyclic base with the compound gives a total yield of the product and the N7-alkylated byproduct of at least 87%, and wherein about 97% of the total yield is the product and wherein about 1.1% of the total yield is the N7-alkylated byproduct.

11. The method of claim 8 wherein the step of reacting the heterocyclic base with the compound gives a total yield of the product and the N7-alkylated byproduct of at least 91%, and wherein about 97% of the total yield is the product and wherein about 1.3% of the total yield is the N7-alkylated byproduct.

12. The method of claim 1 wherein the heterocyclic base is present in the dimethylacetamide at a concentration of up to 220 mM.

13. The method of claim 1 wherein the heterocyclic base is present in the dimethylacetamide at a concentration of up to 270 mM.

14. The method of claim 1 further comprising reacting the product according to Structure 3 with a phosphonate according to Structure 5

Structure 5

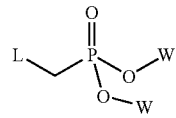

wherein L is a leaving group, and wherein W is a protecting group of the oxygen.

15. The method of claim 14 wherein L is a tosyl group and wherein W is ethyl group.

16. The method of claim 1 wherein Structure 3 is isolated from the dimethylacetamide solvent using tert-butylmethyl-ether.

* * * * *

UNITED STATES PATENT AND TRADEMARK OFFICE
CERTIFICATE OF CORRECTION

PATENT NO. : 7,371,857 B2  Page 1 of 1
APPLICATION NO. : 10/523938
DATED : May 13, 2008
INVENTOR(S) : Kanda Ramasamy et al.

It is certified that error appears in the above-identified patent and that said Letters Patent is hereby corrected as shown below:

Column 4,
Line 64, "—$NH_3+$)" should read -- —$NH_3^+$) --.

Column 12,
Line 24, "W is ethyl group" should read -- W is an ethyl group --.

Signed and Sealed this

Twenty-sixth Day of August, 2008

JON W. DUDAS
*Director of the United States Patent and Trademark Office*